United States Patent [19]

Friedman et al.

[11] Patent Number: 4,891,630
[45] Date of Patent: Jan. 2, 1990

[54] COMPUTER VISION SYSTEM WITH IMPROVED OBJECT ORIENTATION TECHNIQUE

[76] Inventors: Mark B. Friedman, 5539 Darlington Rd., Pittsburgh, Pa. 15217; Gary J. Kiliany, 5030 Centre Ave., Apt. 459, Pittsburgh, Pa. 15213

[21] Appl. No.: 185,062

[22] Filed: Apr. 22, 1988

[51] Int. Cl.[4] .............................................. G09G 3/00
[52] U.S. Cl. ................................... 340/706; 340/712; 340/815.12; 340/825.19
[58] Field of Search ........... 340/706, 711, 712, 815.12, 340/815.13, 815.14, 825.19; 358/93, 103, 104, 105, 107, 125, 126; 250/221, 222.1, 222.2, 223 R, 223 B, 224; 901/46, 47; 364/525

[56] References Cited

U.S. PATENT DOCUMENTS

| | | | |
|---|---|---|---|
| 3,986,030 | 10/1976 | Teltscher | 340/706 |
| 4,109,145 | 8/1978 | Graf | 340/825.19 |
| 4,254,433 | 3/1981 | Dewar, Jr. et al. | 358/105 |
| 4,443,855 | 4/1984 | Bishop et al. | 358/107 |
| 4,648,052 | 3/1987 | Friedman et al. | 364/550 |
| 4,748,502 | 5/1988 | Friedman et al. | 358/93 |

OTHER PUBLICATIONS

"Error Analysis in Stereo Determination of 3-D Point Positions", by Steven D. Blostein and Thomas S. Huang, IEEE Transactions on Pattern Analysis and Machine Intelligence, vol. PAMI-9, No. 6, Nov. 1987, pp. 752-765.

"New Methods for Matching 3-D Objects with Single Perspective Views", by Radu Horaud, IEEE Transactions on Pattern Analysis and Machine Intelligence, vol. PAMI-9, No. 4, May 1987, pp. 401-411.

*Primary Examiner*—Gerald Brigance
*Assistant Examiner*—Jeffery A. Brier
*Attorney, Agent, or Firm*—Webb, Burden, Ziesenheim & Webb

[57] ABSTRACT

A system for computer vision is based upon an image sensor that maps an image to memory cells in association with a computer. An object orientation and position patch is attached to an object to be observed comprising a planar substantially coplanar and non-collinear reflective locations positioned upon the patch and a reflector having the reflective properties of the surface of a regular curved surface intersecting the planar surface. The computer has a task stored in main memory for detecting and quantifying a change in orientation and position of the object from the location of the image of the orientation and position patch.

24 Claims, 4 Drawing Sheets

COMPUTER VISION SYSTEM WITH IMPROVED OBJECT ORIENTATION TECHNIQUE

BACKGROUND OF THE INVENTION

Computer vision systems are systems that analyze camera generated images and enable useful conclusions to be reached from that analysis. Such systems often comprise digitizing an analog image to produce a table of digital data. Thereafter, a digital computer processes the digital data, for example, to locate edges, recognize shapes, or to verify spatial relationships. Eyetrackers are a splendid example of computer vision systems. An eyetracker is a device that measures the movements of the eye upon which the camera is trained. Specifically, an eyetracker detects the direction an eye is gazing. An eyetracker communication system allows the physically handicap person to use eye gaze and movements to communicate. Examples of computer vision systems particularly useful as an eyetracker are set forth in U.S. Pat. No. 4,648,052 entitled "Eyetracker Communication System" and allowed U.S. patent application Ser. No. 06/897,497 entitled "Computer Vision System Based Upon Solid-State Image Sensor." Both of these patent documents disclose an eyetracker wherein the direction of eye gaze is determined by comparison of the location of the center of the image of the corneal reflection and the location of the center of the image of the pupil. While many of the concepts and techniques disclosed in those patent documents are used in the various embodiments of the invention disclosed herein, a drawback in those systems has been overcome. A simple technique is provided for determining the orientation of an object the image of which has been generated by the computer vision system. This technique has application to body pointing in general and robot pickup systems. It has resulted in a substantially improved eyetracker in which it is no longer necessary to locate the image of the pupil.

An eyetracker (eye gaze sensing system) or almost any other computer vision system is improved if the field of view and depth of view of the image are enlarged. In the case of an eyetracker, the larger the field of view, the easier it is to position the device such that the user's eye can be viewed. Maximizing the depth of the field of view is particularly important since it allows the user to be at various positions along the optical axis. One technique for improving the depth of the field is to use an automatic focusing lens, for example, a lens that will mechanically move in order to focus the image of objects at various depths along the optical axis. A mechanical focus is not often desirable. It adds to the expense of the system, adds to the physical size, decreases reliability due to mechanical wear and tear, increases the audible noise generated by the system and slows the eye gaze sensing process during the time when focusing is taking place because the image is blurred at that time. An alternative to an automatic mechanical focusing lens system is to use a fixed focus lens system; that is, a lens focusing an image of an object at only one depth. The depth of field inherent in the fixed focus system is a function of the f number of the lens. The higher the f number, the smaller the diameter of the lens. Also, the higher the f number, the less the capacity to gather light and the larger the depth of field. To maximize the depth of field, the f number must be maximized but this results in less light being gathered by the lens and focused on the image. Hence, to maximize the depth of field by increasing the f number, it is essential to increase the brightness of the image features to be analyzed.

Previous eye gaze sensing techniques have used the position of the corneal reflection relative to the center of the pupil to determine eye gaze location. Because the pupil is very dark, lenses with a low f number have had to be used resulting in an eye gaze system with a small depth of field. To alleviate this problem, the applicants have developed an eye gaze sensing technique that utilizes only bright reflections. The image of the pupil is ignored, thus enabling the use of a lens with a high f number resulting in a large depth of field.

A feature of the applicants computer vision system is a simple technique for determining the three-dimensional (3D) position and orientation of a plane in the field of view. In the case of an eyetracker according to this invention, it is used for determining change in the user's head position.

One prior technique used for determining the position and orientation of an arbitrary plane surface of the object is to view the object with two cameras. Corresponding features of the two images are then matched and a triangulation function is used to determine the distance of the feature points from the cameras. See IEEE PAMI article "Error Analysis in Stereo Determination of 3-D Point Positions", Nov. 1987 and the extensive bibliography of stereo camera literature. Three feature points on a plane serve to uniquely specify the orientation of the plane surface.

Two cameras increase the cost of the system. Therefore, it is desirable to determine the 3D position and orientation of a surface given only one view. This is possible if certain a priori information about the image geometry and behavior of the object to be viewed is available. The image processing literature presents algorithms for extracting 3D information from single perspective views. See, for example, IEEE PAMI article "New Methods for Matching 3-D Objects With Single Perspective Views", May 1987 and the article bibliography. These algorithms are generally concerned with looking at real world scenes and are very computationally intensive. Some of the algorithms use geometric models generated from a CAD data base in order to recognize and locate the corresponding parts in 3D with the machine vision system. These also tend to be very computationally intensive.

According to this invention, a unique reflective patch is attached to the surface whose orientation is to be determined. This results in a simple and inexpensive way to detect 3D orientation and position. In addition, the use of the reflective patch as described herein would reduce the computational complexity of algorithms using two views.

SUMMARY OF THE INVENTION

Briefly, according to this invention, there is provided a system for computer vision based upon an image sensor that maps an image to memory cells in association with a computer. A unique object orientation and position patch is attached to an object to be observed. The position patch comprises a planar substantially nonreflective surface, at least three substantially coplanar and non-collinear reflective locations (a, b, and c) positioned upon the patch and a reflector (d) having the reflective properties of a regular curved surface. The simplest example of a regular curved surface is a spherical surface. The image sensor comprises means for generating a two-dimensional digital representation of the image stored in an array of memory cells arranged in a plurality of rows and columns. The cells each have an associated row and column address and the information at each cell is available for reading. A lens focuses an image of the object including the orientation and position patch upon the image sensor. The lens defines an optical axis extending through the center of the lens and intersecting the image sensor near the center thereof. A light source is fixed relative to the sensor and lens and is directed outwardly therefrom. The system further comprises a computer having a processor and main memory and the capability for reading the row and column addresses of the memory cells corresponding to the images (a', b', and c') of regions a, b, and c and an image (dls) of the light source reflected from the reflector d having the reflective properties of a regular curved surface. The computer has a task stored in main memory for detecting and quantifying a change in orientation and position of the object and, more particularly, a change in orientation and position of the surface upon which the orientation and position patch is secured. The task detects changes in the position along the optical axis and in directions perpendicular thereto by computing changes in the row and column addresses of images a,, b,, and c, The task detects the change in rotation about axes perpendicular to the optical axis by computing differences in the row and column addresses of the image dls and the images a', b', and/or c'.

Preferably, the system for computer vision has a task stored in main memory for detecting and quantifying changes in the position of the object and position patch along the optical axis by computing the average of the changes in distance between the addresses of images a', b', and c' as represented by the differences in row and column addresses upon the image sensor and interpreting a decrease in the average as a movement away from the lens. Preferably, according to this invention the task stored in the optical axis by computing the average of the changes in row or column addresses of the images a', b', and c'. Preferably, according to this invention, the task stored in main memory detects changes in the rotation of the object about axes perpendicular to the optical axis by computing differences in the row or column addresses of at least one of the images a', b', c', and the row or column address of the image dls. Preferably, the system for computer vision has a task stored in main memory for detecting and quantifying a change in the rotation about an axis parallel to the optical axis by observing the change in row or column addresses of at least one of the images a', b', c' and interpreting the directions of movements of said images as tangent to concentric circles about the axis of rotation.

According to a preferred embodiment of this invention, the system for computer vision comprises a solid-state image sensor having a two-dimensional array of light sensitive memory cells upon which the lens focuses the image. The computer vision system described so far may comprise the heart of any number of specific purpose computer vision systems, for example, a body pointing system, a robot pickup system, or an eyetracker. A body pointing system comprises a system that recognizes the orientation of a body within the field of view of the computer vision system and may, for example, comprise a system for detecting head orientation, finger orientation, or the orientation of an inanimate part upon an assembly line. A robot pickup system is a system for picking up parts comprising a robot arm and a computer vision system as disclosed herein. The computer vision system is used to determine the orientation of the part to be picked up and the robot arm is then controlled to approach the part from a selected direction.

An eyetracker according to this invention comprises a computer vision system as already described. Additionally, it comprises a display bearing an indicia which may be selected with the user's eyes. The display is typically mounted to surround the image sensor. The unique head orientation and position patch is attached to the face of the user near an eye. The computer has a first task stored in main memory for calibrating the eyetracker for an initial head orientation and position. The user looks sequentially toward at least two of the indicia upon the display while the head is substantially immobile. At each position the row and column addresses of the images a', b', c', dls and cls are recorded. The image cls is the reflection of the light source from the cornea of the eye of the user to the image sensor. The computer has a second task stored in main memory for detecting and quantifying a change in head orientation and position as aforedescribed for the basic computer vision system. The computer has a third task stored in main memory for correlating the row and column addresses of the corneal reflection image cls with indicia upon the display taking in consideration the head position and orientation as determined by the first task and the change in head position and orientation determined by the second task.

DESCRIPTION OF THE DRAWINGS

Further features and other objects and advantages will become clear from the following detailed description made with reference to the drawings in which.

DESCRIPTION OF THE PREFERRED EMBODIMENTS

Figure 1:
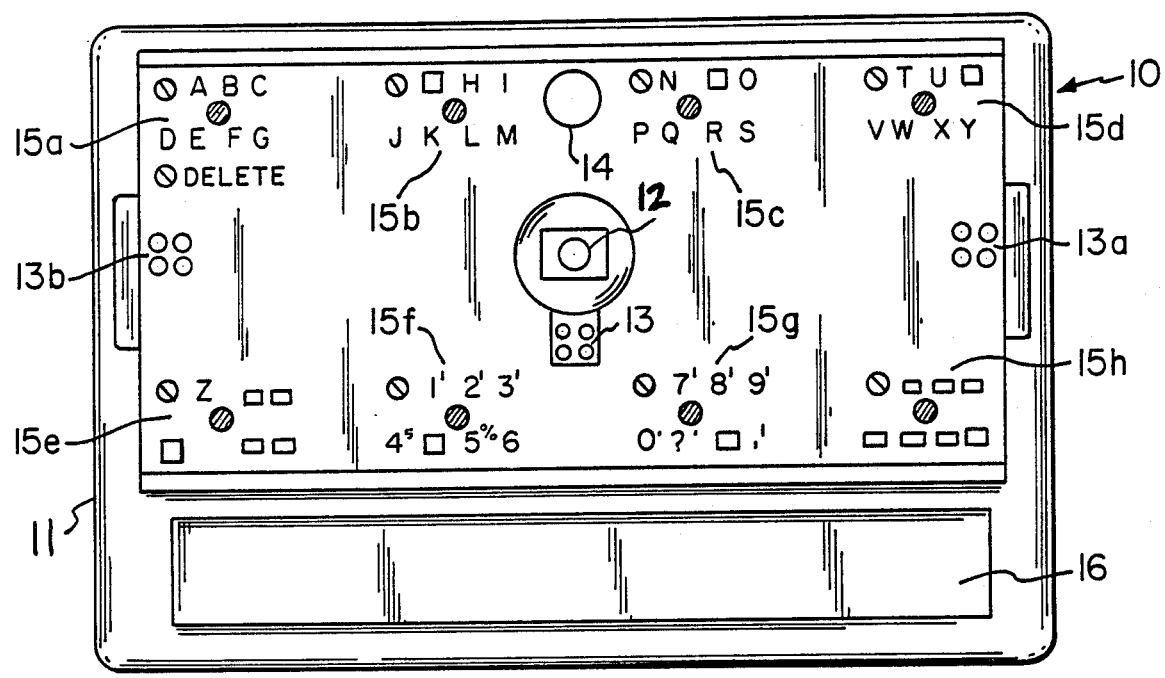
FIG. 1 is a front view of a "keyboard" used in an eyetracker embodiment of this invention.

Referring now to FIG. 1, there is shown the front view of the board of an eyetracker communication system. The entire system has been implemented to fit an 8 by 12 by 3 inch case 10 and to weigh less than five pounds. The front of the case 11, referred to as the "board" or "keyboard", has mounted therein a lens 12 and a plurality of infrared lights 13 near the lens. The lights are directed outward from the keyboard. An image sensor, for example, CCD solid-state image sensor is positioned behind the lens. A set-up light 14 is mounted at the top edge of the keyboard to direct a narrow visible beam of light perpendicular to the keyboard. The keyboard can then be easily positioned relative to the user by locating the beam spot above an eye on the forehead of the user.

The keyboard is provided with eight eye gaze positions (15a to 15h) with indicia of up to eight characters or functions located at each position. An acknowledge light may also be located at each position. In one mode of operation, a character or function may be established by the double gaze technique. In other words, the user gazes first at one of the positions containing the desired character of function. Then, the user gazes at the position on the keyboard which corresponds to the position of the indicia desired relative to the first position. For example, to select the character "A" the user would first gaze at the position 15a in the upper left-hand corner, and then gaze again at position 15b. As a further example, to select the character "G" the user would first gaze at the position 15a in the upper left-hand corner and then at the position 15h in the lower right-hand corner. The acknowledge lights simply indicate the location of the gaze. When the gaze has been held long enough to make a selection a tone is emitted. This length of time, called "dwell time", can be varied by the user to be short (½ second) or long (4 seconds).

A forty character display 16 is provided along the bottom of the keyboard to display characters that have been selected and words and sentences as they are assembled. The words or sentences may be dispatched to a printer, for example, with a carriage return. The possibilities are unlimited. The eyetyper may actually have associated word processing software for the case where the user desired to prepare a substantial amount of text. In the more usual and essential case of making possible the most basic of communication, the sentence may be dispatched to a speech synthesizer to actually speak the message.

In another mode of operation, the vision system is preprogrammed with short messages associated with each eye gaze position. These may be selected by a single gaze.

The image of the eye formed by the lens 12 upon the image sensor is analyzed to determine the direction of gaze. The specific means of detecting which of the eight eye gaze positions is being looked upon is a variation of the corneal reflection technique. Basically, the system detects the position of the corneal reflection relative to the position of the head. The position of the corneal reflection can be correlated to the position being gazed upon.

Figure 2:
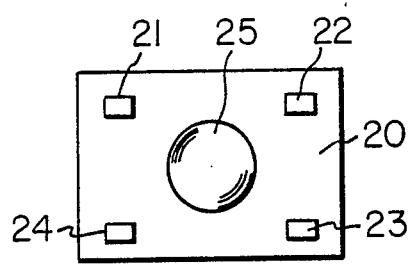
FIG. 2 is a front view of an orientation and position patch according to one embodiment of this invention.

In order to determine the 3D orientation and position of a user's head (generalizing to a plane surface) with a single view and with an inexpensive 8 bit microprocessor, a reflective patch 20 is attached to the user's face with double stick tape. The physical design of the patch is shown in FIG. 2. There are four spots (0.1" squares) 21, 22, 23 and 24 of retroreflective material (3M type 8610, for example) positioned in the corners of the patch. In the center of the patch is a 0.5" diameter spherical plastic bubble 25 whose radius of curvature is 7/16". When the user is in front of the eyetyper, the infrared light emitting diodes beneath the camera lens are reflected from the front surface of the plastic bubble back to the camera lens. A small, bright reflection from the surface of the spherical plastic bubble 25 results from the fact that the bubble acts as a spherical reflector. As the patch is rotated or translated left or right the reflection moves left or right. As the patch is rotated or translated up or down the reflection moves up or down. The rotation effect is much larger than the translation effect. It should be emphasized that the reflective patch is a passive reflector as opposed to the active transponders/transducers used in other multi degree of freedom orientation sensing systems. In the general case, the technique being described required only 3 coplanar spots. Any one of reflectors 21, 22, 23, 24 could be eliminated. The spherical bubble could be replaced by flat fresnel lens, a conventional lens, a curved mirror (concave or convex), or reflective material physically elevated above the plane. With current optical technology, the curved optical elements may be replaced with their flat holographic equivalent. Obviously multiple reflective devices can be attached to any object to extend the range of motion an object may undergo and still be sensed from a given viewpoint. A spherical reflector, as described in the preferred embodiment, can minimize the computational complexity of head orientation compensation for eye gaze sensing purposes. Other curved surfaces may be used. Preferably, the curved surface is symmetrical with respect to two perpendicular planes the intersection of which defines a line perpendicular to the patch. The specific physical separation between the reflective spots and, therefore, the size of the device can be varied for different application specific reasons (e.g. different lens-camera arrangements). Rotational ambiguities as a result of severe rotations of the reflective device can be dealt with by having each of the reflective spots uniquely identifiable (e.g. different sizes, shapes, colors, etc.). In the general case, the coplanar spots need not be discrete. It is only required that a planar region whose center can be distinguished and whose perimeter is distinct be imaged. The preferred embodiment uses four retroreflective coplanar spots and a plastic bubble to generate a fifth elevated point. This is done to simplify fabrication of the reflective patch, to ease the image processing requirements, and to provide redundancy in the orientation computations for noise immunity purposes.

Figure 3:
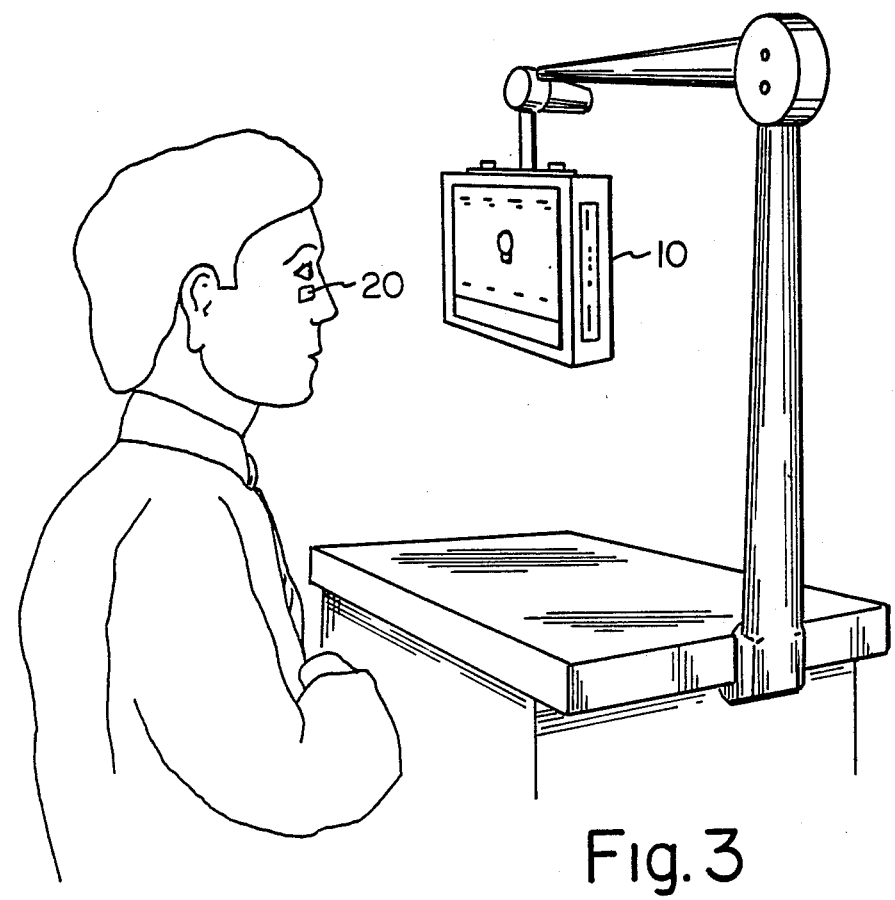
FIG. 3 is a perspective view of a user using an eyetracker according to this invention.

FIG. 3 shows the relation of the board 10, the user and the patch 20 when the computer vision system is being used as an eyetyper. The patch is worn by the user just below one eye. Double stick tape may be used to hold the patch in place.

Figure 4:
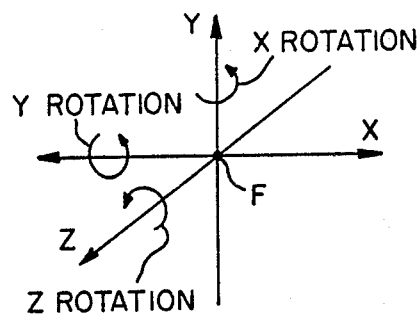
FIG. 4 is a diagram for explaining the coordinate system used to explain the use of the orient and position patch.

Referring to FIG. 4, the coordinate system used throughout this discussion has its origin at the focal point F of the lens that forms an image of the eye and patch. The image plane is parallel to the xy-plane at distance f (the focal length) from the origin along the z axis. So, as the user sits in front of the eyetyper and moves left and right he moves along the x axis; as the user moves up and down he moves along the y axis; as the user moves in and out he moves along the z axis.

The head rotating left and right (rotation about the y axis) is referred to as x rotation because this rotation direction predominantly affects the horizontal eye gaze selection location (x location). Rotation up and down (about the x axis) will be referred to as y rotation because this rotation direction predominantly affects the vertical eye gaze selection (y location). Rotation about the z axis will be referred to as z rotation.

It is important to recognize, for eye gaze sensing purposes, that the human physiology makes it much easier for a person to rotate their head left and right (x rotation) than to move in any other direction. This makes head x rotation changes the major effect that must be compensated for when attempting to determine the location of a person's gaze.

Figure 5:
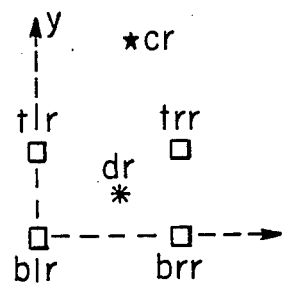
FIG. 5 is a diagram for understanding the elements of the image of the orientation and position patch upon the image sensor.

For the computation of head orientation from a single view of the reflective patch, the 5 spots as shown in FIG. 5 will be referred to as tlr (top left region), trr (top right region), blr (bottom left region), brr (bottom right region) and dr (dome region). The x position of a spot is referred by an ".x" following the designation of the region, for example, "tlr.x" Likewise, "tlr.y" is reference to the y position of region tlr. Also shown on FIG. 5 is the corneal reflection, "cr", which is not an image caused by the patch and will be explained hereafter. The image processing hardware and software extracts the 5 regions from a single camera image and computes the x and y positions of the center of each spot.

Determining the x and y translation of the patch is very straightforward. One can simply compute change in the average of the x and y centers of the four corner regions.

$$x \text{ position} = \frac{tlr \cdot x + trr \cdot x + blr \cdot x + brr \cdot x}{4}$$

$$y \text{ position} = \frac{tlr \cdot y + trr \cdot y + blr \cdot y + brr \cdot y}{4}$$

If there are no rotations, the z position (distance of the user from the camera lens) can be computed by using one of four differences: y difference between the y centers of the trr and brr regions; y difference of tlr and blr regions; x difference of blr and brr regions; and x difference of tlr and trr regions.

z position=(tlr.y−blr.y) or (trr.y−brr.y) or (tlr.x−trr.x) or (blr.x−brr.x)

As the user moves in and out these differences will all expand and contract proportionately. Using 4 coplanar points instead of the minimum required 3 points there exists redundancy since the x distances should be identical and the y distances should be identical. This can be used to increase immunity to noise in the imaging system.

If there is x rotation then one should use the y differences as a measure of z position. If there is y rotation then one should use the x differences as a measure of z position. For many rotations it is possible to measure them and compensate for the inaccuracies they introduce into the z position measure. In the preferred embodiment, if there are large x and y rotations then it is difficult to extract the z position information. In cases of large rotations of the orientation and position patch or of the cornea of the eye in the case of an eyetracker, the reflected image of the light source may move off of the image sensor. To compensate for this loss of the image of the light source, one or more secondary geometrically displaced light sources (13a and 13b in FIG. 1) may be turned on under computer control. If the image from one of the secondary light sources falls upon the image sensor, large x and y rotations may be compensated. Another manner of dealing with such large rotations would be to provide multiple spaced image sensors.

In the general case, where there may be a rotationally invariant reflective perimeter defining the primary plane (an annulus around the non-coplanar reflector), this restriction is not as severe. Fortunately, in the application domain of the preferred embodiment, this is infrequent because the human head usually does not move significantly.

Since the reflection off of the plastic bubble moves left and right as the patch is rotated, it can be used to measure x rotation (head rotating left and right). Taking the ratio of (brr.x−dr.x) and (dr.x−blr.x) or the ratio or (trr.x−dr.x) and (dr.x−tlr.x) can give a z position invariant measure of x rotation since the differences will expand and contract in proportion as the z position changes.

$$x \text{ rotation} = \frac{brr \cdot x - dr \cdot x}{dr \cdot x - blr \cdot x} \text{ or } \frac{trr \cdot x - dr \cdot x}{dr \cdot x - tlr \cdot x}$$

These differences must be computed relative to the origin of the patch which may be taken on blr in order to make the measure invariant to z rotation. X translation also affects the position of the reflection off of the plastic bubble but the rotation effect greatly dominates the translation effect. Since it is very easy to know the translational position of the patch, and the imaging geometry is known (position of light source that causes the reflection), it is very easy to compensate for the translational effects on the measure of x rotation.

The y rotation measure (head rotating up and down, generally, about the axis defined by a line going straight from one ear to the other through the head) is a direct corollary of the x rotation measure. Since the reflection off of the plastic bubble moves up and down as the patch is rotated, it can be used to measure y rotation. Taking the ratio of (dr.y−trr.y) and (brr.y−dr.y) or the ratio of (dr.y−tlr.y) and (blr.y−dr.y) can give a z position invariant measure of y rotation since the differences will expand and contract in tandem as the z position changes.

$$y \text{ rotation} = \frac{dr \cdot y - trr \cdot y}{brr \cdot y - dr \cdot y} \text{ or } \frac{dr \cdot y - tlr \cdot y}{blr \cdot y - dr \cdot y}$$

These differences must be computed relative to the origin of the patch (bottom left region) in order to make the measure invariant to z rotation.

Y translation also affects the position of the reflection off of the plastic bubble but the rotation effect greatly dominates the translation effect. Since it is very easy to know the translational position of the patch, and the imaging geometry is known (position of light source that causes the reflection), it is very easy to compensate for the translational effects on the measure of y rotation.

The z rotation or head "tilt" can be measured by using x differences or y differences. These differences must be z scaled, i.e., they must be normalized to a common z position reference since a change in z position will make the differences larger or smaller. This z position normalization can be performed by multiplying the x differences by the amount that they expand or contract relative to the "normal" reference and multiplying the y differences by the amount that they expand or contract relative to the "normal" reference.

z rotation or "tilt" = (blr · y − brr · y) or (tlr · y − trr · y)
  or (tlr · x − blr · x) or (trr · x − brr · x)

Figure 6:
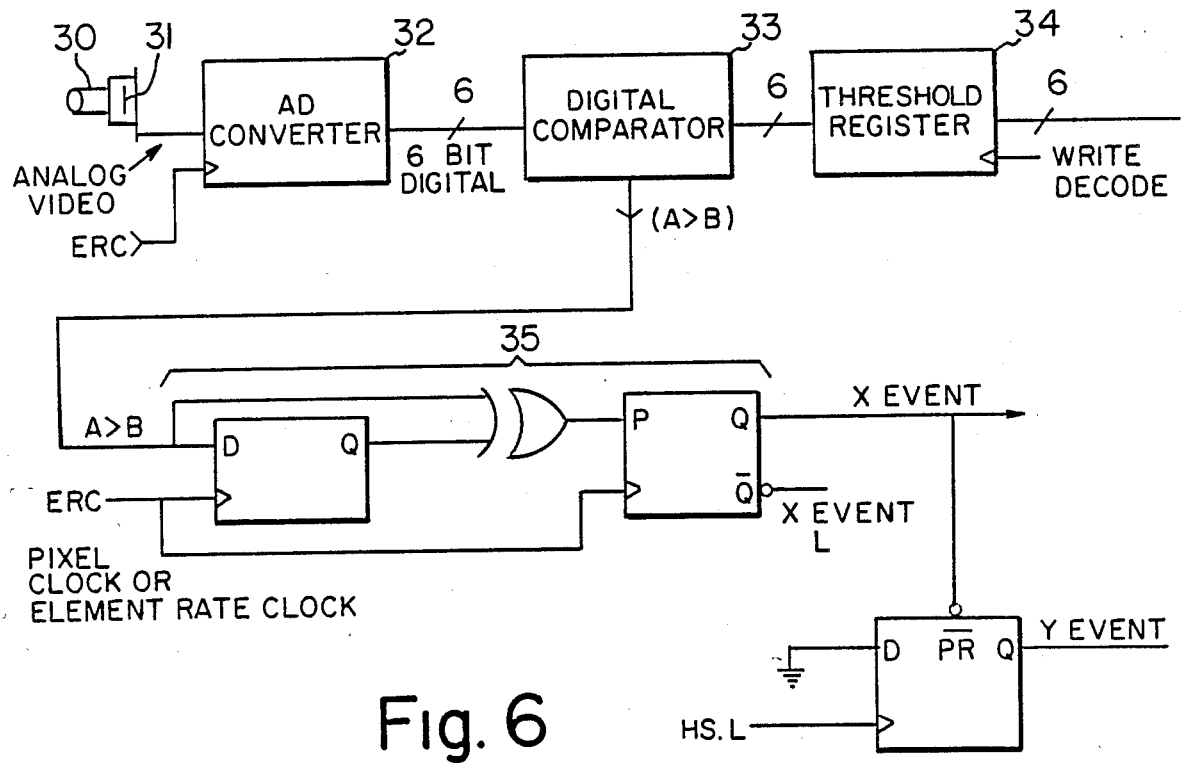
FIGS. 6, 7 and 8 are schematic diagrams for explaining the hardware that captures the information on the image sensor for transfer to the computer.

Most modern, automated, eye gaze sensing methods include some type of image sensor upon which an eye is focussed, a light source that illuminates the eye, and a computer which processes the information from the image sensor in order to determine where the eye is gazing. Referring to FIG. 6, the system disclosed herein has been constructed and uses a 16 mm camera lens 30, a 298,000 pixel solid-state CCD (charge coupled device) image sensor 31, infrared light emitting diodes, and an inexpensive 8 bit microprocessor. The analog video output of the CCD camera is digitized by an analog-to-digital converter 32 whose output is connected to a digital comparator 33. The comparator generates a signal called "A>B" when the digital value representing an individual pixel is greater than the value stored in an 8 bit register called the threshold register 34. This single level thresholding effectively converts a multiple gray level analog image into a binary image, i.e., an image with only 2 levels (black or white). This threshold register is programmable by the software and is adjusted dynamically in order to obtain the best separation of the reflective patch and corneal reflection from the user's face. An alternative to dynamic thresholding of cornea and patch, is to vary the integration times of image sensor regions (frame, line, or pixel based). In the preferred embodiment, dynamic single level thresholding results in the device being much more robust to widely varying lighting conditions. While the preferred embodiment uses binary thresholding image economy, gray scale image processing may be used to extract the key features from suboptimal or noisy images.

The CCD camera also generates digital horizontal (HS) and vertical (VS) synchronization pulses that conform to the RS-170 video standard. A 10 MHz element rate clock (ERC) or pixel clock is also generated. This serves to synchronize the analog-to-digital convertor with the rest of the video processing logic. The $A \approx B$ signal goes to a small, digital edge detecting circuit 35 which generates a signal called "x event" indicating the beginning or end of a thresholded line segment. X event presets a flip-flop which generates "y event".

Figure 7:
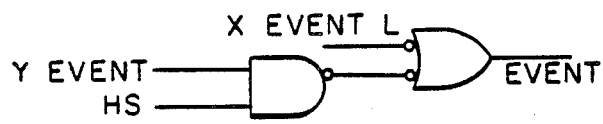

Referring to FIG. 7, the x event and y event signals are combined to generate a single digital signal called "Event". This signal causes the location of an edge (detected in the binary image) to be stored in a FIFO (first in first out) memory. The microprocessor can then read the numbers representing the location of the edges from the FIFO memory.

Figure 8:
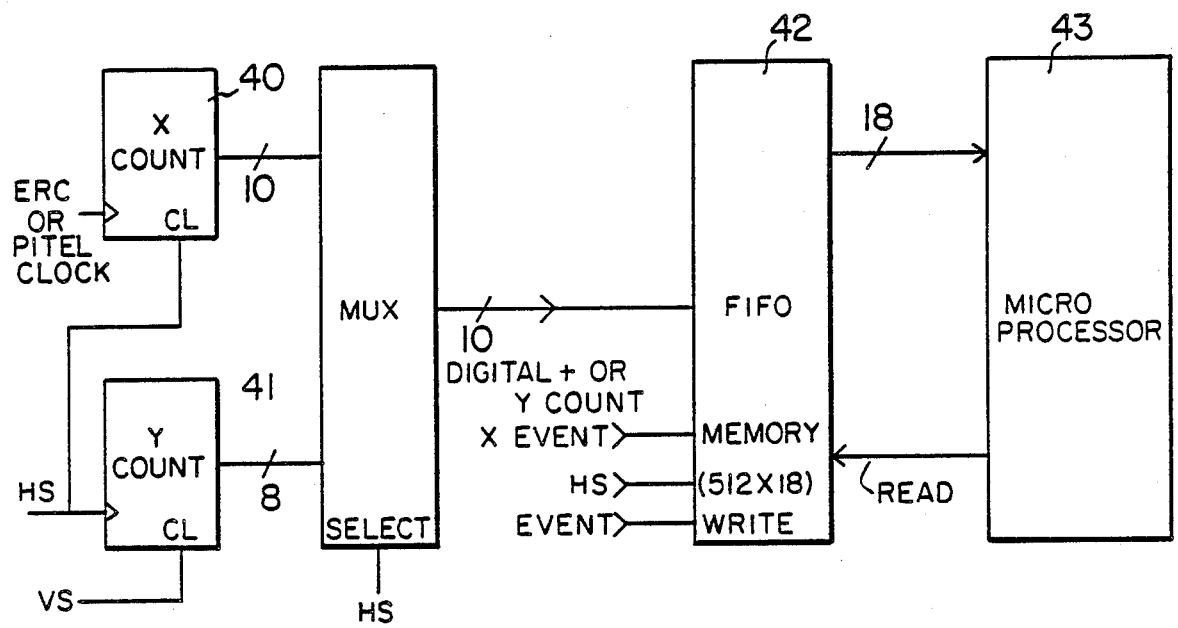

FIG. 8 shows the way that the ERC and HS signals from the camera are used to clock two synchronous, binary counters 40, 41 whose counts will be stored in the FIFO memory 42 indicating the location of an edge in the binary image. The EVENT signal causes the FIFO memory to store the information presented at its inputs. The eye gaze processing microprocessor 43 can then read this information via its data bus by asserting a read signal.

Figure 9:
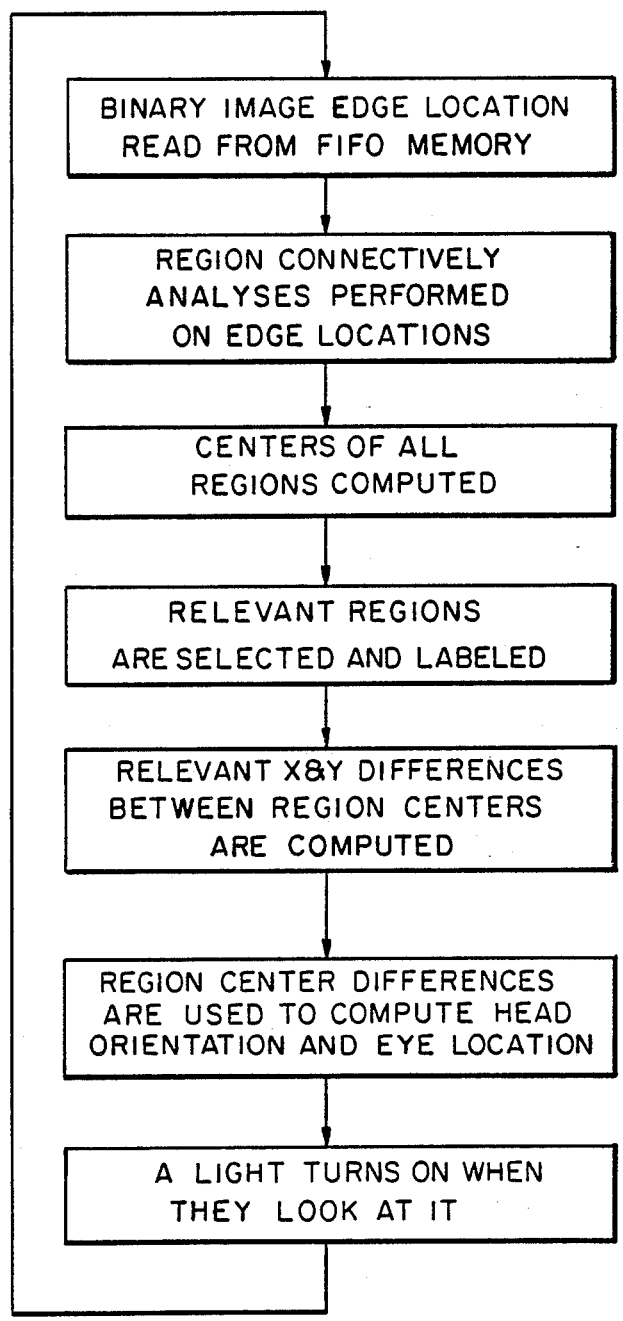
FIG. 9 is a flow diagram for explaining the software use interpreting the image upon the image sensor.

The microprocessor has stored tasks (software) for implementing the image analysis. Referring to FIG. 9, the software reads the locations of edges in the binary image from the FIFO memory and performs a standard, binary image region connectivity analysis. The x and y centers of all regions resulting from the connectivity software are then computed. Next, regions representing the patch reflections and the corneal reflection are selected and labeled. The x and y differences between the centers of regions that are necessary to compute the user's head orientation and point of gaze are then computed.

As already explained, the user wears a reflective patch beneath their eye and sits in front of the image of the camera lens. When the eyetracker is turned on, the user goes through a 2 position calibration sequence. He looks at the top left selection position and then the bottom right selection position. After this calibration, the user can select any position on the front panel of the device by simply looking at it. The computer calculates and remembers the position and orientation of the patch and the corneal reflections during the calibration. As the user's head moves, the computer computes the head position and orientation changes and modifies its corneal reflection to gaze point mapping appropriately. By using the position of the corneal reflection relative to the reflective patch, the calibration information, and information about the position and orientation changes since calibration of the reflective patch (which is attached to the user's head), the user's gaze point can be determined.

The head orientation, eye gaze transform module (software listing attached as Appendix A) computes the x_ selection (0 to 3) and y_ selection (0 to 1) of the user's gaze on the display. The final output is the variable called "selection" which is an integer number from 1 to 8 representing which of the 8 positions on the display the user is looking at. These software algorithms can be directly extended to selection displays with many more eye gaze positions. The number of positions ultimately chosen is limited by the resolution of the imaging system, the anatomical location of the reflecting patch, the patch geometry and size, eye physiology (e.g., physical distance that the corneal reflection moves) amount of noise in the region to region distance measurements, and other high level human-machine interaction considerations.

The head orientation transforms modify the x_ midline and y_ midline variables which indicate what the software believes the x distance between the image of the corneal reflection cr and the image dr and the y distance between the image cr and the image dr would be if the user were looking at the exact center selection display, given the current head position and orientation. X_delta is the x (horizontal) distance (in terms of number of pixels) that the corneal reflection would move between gazing at adjacent x selections on the display. As the user moves closer to the camera (z position change), all the x and y distances get larger. As the user moves farther away, all the distances get smaller. Therefore the y midline and x delta get larger or smaller accordingly. As the user rotates his head left and right horizontally, the x midline must slide left and right. This is also the case for x translation although it is a much smaller affect.

In an alternate embodiment, the orientation and position of a person's head itself can be used to make selections on the display. In fact, the computer vision systems disclosed can be used as a headpointer, as well as, an eye gaze controlled communication device. The advantage over existing headpointing methods is that the reflective patch is passive, i.e., it is not an active transponder system. More generally, any body part to which the patch is secured can be used as the pointer. The user of the eyetyper may type messages letter by letter which appear on the 40 character display 16 (see FIG. 1), or select one of several previously programmed messages. The messages selected or typed can be spoken by a built in speech synthesizer or sent to a printer, computer, or environmental control device through its RS-232 connector, etc.

The following pages are annotated source code used to implement the best mode of the eyetracker described herein.

```
/*
 *      headxf_shadow.c          V 1.10
 *
 *                  Author: Gary Kiliany
 *              Sentient Systems Technology Inc. (SST)
 *
 *      This software module is written in the C programming language.
 *      It takes as input the various x and y differences between the
 *      bright spots used for the EyeTyper-300. A group of spots is used to determine the
 *      orientation of the user's head and the corneal reflection is used to determine
 *      the position of the user's eye within the head. This software determines the gaze
 *      point of the user on the EyeTyper-300 selection area given the differences between
 *      the various bright spots.
 *
 *
 *
 *      The various bright spots are designated as follows.
 *
 *
 *                          (CR)      Corneal reflection
 *
 *
 *
 *      top left region (TL)          (TR)     top right region
 *
 *                          (DR)               plastic dome region
 *
 *   bottom left region (LR)          (BR)     bottom right region
 *
 *      The various x and y distances between the 6 regions are taken as inputs. These
 *      differences are computed by the image processing software.
 *      A variable called tr_br_y would represent the difference between the y centers of
 *      the top right region and the bottom right region.
 *      Variable names beginning with "cal_" are attributes computed right after the
 *      user completes the 2 position calibration sequence. The user looks at the top
 *      left selection position and then the bottom right selection position when prompted
 *      to by the EyeTyper's built in speech synthesizer.
 *      The bottom five regions are used for the head orientation determination.
 *
 *      The module computes the x_selection (0 to 3) and y_selection (0 or 1) of the
 *      user's gaze on the EyeTyper 300 display. The final output is the variable called
 *      "selection" which is an integer number from 1 to 8 representing which of
 *      the 8 lights the user is looking at on the EyeTyper 300 display.
 *
 *      The orientation transforms modify the x_midline and y_midline variables which
 *      indicate what the software believes cr_dr_x and cr_dr_y would be if the user
 *      were looking at the exact center of the EyeTyper 300's selection display given
 *      their current head position and orientation. x_delta is the x (horizontal) distance
 *      that the corneal reflection would move between gazing at adjacent x selections on
 *      the EyeTyper 300 display.
 *      As the user moves closer to the EyeTyper's camera (z position change),
 *      all the x and y distances get larger. As the user moves farther away, all the
 *      distances get smaller.
 */
/*      Declarations for this module. */ define MIN_TR_BR 36         /* constants */
define MAX_TR_BR 60    /* minimum and maximum values for the tr_br_y distance. */
#define X_NORMALIZER 128 /* used to eliminate negative x differences for x selection*/

/* differences between the various bright spots */
int tr_br_y, dr_br_x, dr_br_y, cr_dr_x, cr_dr_y,
 tr_br_x, lr_br_x, dr_tr_y, dr_lr_x, lr_br_x,  tl_bl_y;

int head_x, head_y;       /* absolute x and y head position */
int cal_head_x, cal_head_y; /* x and y head position during calibrate */

/* differences generated during the two point calibration   */
int cal_tr_br_y, cal_dr_br_y, cal_dr_tr_y, cal_tl_bl_y,
       cal_dr_br_x, cal_dr_lr_x, cal_lr_br_x, cal_tr_br_x;
```

```
int cal_x_left, cal_x_right; /* cr_dr_x differences for top left calibrate position
                                 and bottom right calibrate position */
int cal_top, cal_bottom;      /* cr_dr_y differences for top and bottom positions */ float cal_z_position; /* user's z position during calibration */
float z_position;     /* measure of user's current z position */ float cal_x_rotation;    /* x rotation of user's head during calibration */
float x_rotation_change; /* measure of how much user's head x rotated since calibration*/
int x_rotation;          /* current horizontal head rotation */
int x_rotation_index;    /* integer derived from x_rotation_change used to index into table
                            used to move the x_midline based on head rotation */
int xrotation_movement;  /* how much x rotation has changed since last gaze selection */ int x_translation, y_translation;  /* amount head translated since calibrate */
float z_movement; /* z translation since last eye gaze selection */ int head_tilt;  /* amount of head tilt (rotation about the z axis ) */

/* eye gaze selection location computed by this software */
int selection, y_selection, x_selection;

float y_midline;       /* used as the y selection center line to determine the y sel */
float x_midline;       /* used as the x selection center line to determine the x sel */
float cal_y_midline;   /* y midline calculated from calibration sequence */
float cal_x_midline;   /* x midline calculated from calibration sequence */
float x_delta;         /* horizontal distance between adjacent eye gaze x selections */ float z_ymid_table[80];  /* table of all possible y_midlines indexed by z position*/ float float_tr_br_y;

/* Variables beginning with "prev" are attributes saved between consecutive eye gaze
selection computations. We use them for noise immunity purposes and to detect sudden
head orientation chages */ int prev_tr_br_y, prev_tl_bl_y, prev_x_rotation, prev_xrot_index;
float prev_z_position;

/***********************************************************************
*       init_headxf is called immediately after the user finishes the 2 point
*       calibration sequence. It uses the region distances found to initialize
*       the eye gaze mapping variables and calls routines that initialize head
*       orientation transform tables.
*/
init_headxf( )

{
        cal_z_position = (cal_tl_bl_y + cal_tr_br_y) / 2.0;

/*compute y midline from calibrate y differences */
        cal_y_midline = (cal_top + cal_bottom )/ 2.0;

get_x_delta( );  /* set up x_delta for the z position used during cal*/ cal_x_midline = (cal_x_left + cal_x_right) / 2.0; /* compute initial x midline */ dr_lr_x = cal_dr_lr_x;
        dr_br_x = cal_dr_br_x;
        compute_xrot( );       /* compute head x rotation position used during cal */
        cal_x_rotation = x_rotation;
        prev_x_rotation = x_rotation;

build_ymid_table( );   /* build table of y midline values indexed by z position */
}
```

```
/****************************************************************
 *       compute_selection calls all the head orientation gaze mapping transforms
 *       and uses their output to compute the eye gaze selection. It is called every time
 *       a new set of inter-region distances is available.
 *       The orientation transforms modify the x_midline and y_midline variables which
 *       indicate what the software believes cr_dr_x and cr_dr_y would be if the user
 *       were looking at the exact center of the EyeTyper 300's selection display given
 *       their current head position and orientation.
 */
compute_selection( )
{
        compute_z_position( );   /* determine user's distance from front panel */
        z_movement = z_position - prev_z_position;
        ysel_z_transform( );     /* move y_midline based on z position of user. */

/* compute amount of y translation of user's head since calibration */
        y_translation = cal_head_y - head_y;

/* determine y selection by computing whether cr_dr_y is above or below the y_midline */
        if ( cr_dr_y > y_midline) /* see if y difference is above or below midline */
                y_selection = 0;        /* top y selection */
        else
                y_selection = 1;        /* bottom y sel */

/* NOW FIND THE X SELECTION using cr_dr_x*/
/* compute amount and direction of head, horizontal translation since calibration */
        x_translation = cal_head_x - head_x;  /*translation is used to effect rotation measure
/* determine how much the user's head rotated since calibration */
        get_xrot_change( );

xsel_z_transform( );     /* transform x_midline and x_delta for z axis */
        xsel_x_translation( );   /* transform x_midline for head translation */
        xsel_x_rotation( );      /* transform x_midline for head rotation */
        xrotation_movement = absval( x_rotation_index - prev_xrot_index);
        xsel_head_tilt( );       /* transform x_midline for head tilt */ if (cr_dr_x >= 128)              /* convert signed hex number to signed decimal numbe
                cr_dr_x = cr_dr_x - 256;
        cr_dr_x += X_NORMALIZER;         /* normalize raw x difference */

/* map cr_dr_x to an x selection given x_midline and x_delta */
        if (cr_dr_x > x_midline)
                x_selection = 2 + (int) ((cr_dr_x - x_midline) / x_delta);
        else
                x_selection = 1 - (int) ((x_midline - cr_dr_x) / x_delta);

if (x_selection < 0)
                x_selection = 0;
        if (x_selection > 3)
                x_selection = 3;

/* map x selection (0..3) and y selection (0..1) to selection number (1..8) */
        selection = (y_selection * 4) + 1 + x_selection;

/* remember what region distances were for the next sample */
        prev_tr_br_y = tr_br_y;
        prev_tl_bl_y = tl_bl_y;
        prev_z_position = z_position;
        prev_x_rotation = x_rotation;
        prev_xrot_index = x_rotation_index;
}
/*
 *       compute_z_position uses tr_br_y and tl_bl_y to generate a measure of the user's
 *       z_position (distance away from the front panel).
 *       We use the two measures in a redundant fashion in order to increase our
 *       immunity to noise.
 */
compute_z_position( )
```

```
{
int left_deriv, right_deriv;

left_deriv = tl_bl_y - prev_tl_bl_y;
        right_deriv = tr_br_y - prev_tr_br_y;

if ((absval(left_deriv) > 1) && (absval(right_deriv) < 2 ))
            z_position = tr_br_y;
        else if ((absval(right_deriv) > 1) && (absval(left_deriv) < 2 ))
            z_position = tl_bl_y;
        else
            z_position = (tr_br_y + tl_bl_y) / 2.0 ;
}

/*
 *      ysel_z_transform takes the z_position of the user's head, computes an
 *      index into the table that holds all possible values of the y_midline, and
 *      pulls out that proper y_midline value.
 */
ysel_z_transform( )

{
int ymid_index;

/* average adjacent z_position measures and compute index into y midline table */
        if ( ((absval(z_position - prev_z_position)) < 4) )
            ymid_index = z_position + prev_z_position - (2 * MIN_TR_BR);
        else
            ymid_index = 2 * (z_position - MIN_TR_BR);

if ( ymid_index < 0 )   /* make sure index is within a correct range */
                ymid_index = 0;
        if (ymid_index >= (2 * (MAX_TR_BR - MIN_TR_BR - 1)))
                ymid_index = 2 * (MAX_TR_BR - MIN_TR_BR - 1);

y_midline = z_ymid_table[ymid_index];   /* y midline value out of table */
}
/*
 *      compute_z_ymid generates a new value for the y_midline given the current tr_br_y
 *      cal_tr_br_y, and cal_y_midline. As the user moves closer to the EyeTyper
 *      tr_br_y gets larger and the y_midline must get larger. The inverse is also true.
 */
compute_z_ymid( )
{
        y_midline = ( float_tr_br_y / (float) cal_z_position)  * ((float) cal_y_midline);
}

/*
 *      build_ymid_table computes the y_midline for every possible tr_br_y (z_position)
 *      and stores the result in a table called z_ymid_table. By storing all possible
 *      values in a table, we decrease the amount of time needed for this part of the
 *      eye gaze location calculation.
 */
build_ymid_table( )

{
int foo_index;

foo_index = 0;
        for (float_tr_br_y = (float) MIN_TR_BR; float_tr_br_y < (MAX_TR_BR + 1);
        float_tr_br_y += 0.5) {
                compute_z_ymid( );
                z_ymid_table[foo_index] = y_midline;
                foo_index++;
        }
}
```

```
/*
 *      compute_xrot generates a measure of x_rotation based on dr_lr_x and dr_br_x.
 *      x_rotation is an 8 bit integer representation of a 3 bit integer part 5 bit fractio
 *      part result.
 */
compute_xrot( )

{
        x_rotation = ( 256 * dr_lr_x) / dr_br_x;
        x_rotation = x_rotation / 8;
}

/*
 *      get_xrot_change computes the amount that the user's head has rotated horizontally
 *      (left vs right) since calibration. It also computes the x_rotation_index which is
 *      used in xsel_x_rotation to compensate for this axis of head movement.
 */
get_xrot_change( )

{
        compute_xrot( );        /* compute first approx of head x rotation */

/* compute x_rotation_change. average adjacent x_rotation measures */
        x_rotation_change = cal_x_rotation - ((int) ((x_rotation + prev_x_rotation) / 2));
        x_rotation_change += 128;  /* normalize rotation change to all positive */

/* now modify x_rotation_change measure based on how much x_translation there has been */
        x_rotation_change = x_rotation_change + (x_translation / 2.90);

/* compute x_rotation_index from x_rotation_change measure */
        x_rotation_index = (x_rotation_change / 4) - 16;
/*
 *      xsel_z_transform makes sure the x_delta for the current z_position is
 *      computed and initializes x_midline so it can be modified by the head
 *      transform routines.
 */
xsel_z_transform( )

{
        get_x_delta( );  /* set up x_delta for the current z position */

/* initialize x_midline so other head orientation transforms can modify it */
        x_midline = cal_x_midline;
}

/*
 *      xsel_x_translation moves the x_midline left or right depending on
 *      how much x translation of the user's head there has been since the calibration.
 */
xsel_x_translation( )

{
        x_midline = x_midline - (x_translation / 35.0);
}

/*
 *      xsel_x_rotation modifies the x_midline based on how much horizontal ( left or right
 *      head rotation there has been since calibration.
 *      The x_rotation_index was computed by get_xrot_change.
 */
static float x_rotation_table[] = {
                -10.0, -10.0, -9.0, -9.0, -8.0,  /* 0-4 */
                -7.0, -7.0, -6.0, -6.0, -5.0,    /* 5-9 */
                -4.0, -3.5, -3.0, -2.5, -2.0,    /* 10-14 */
                -1.0, 0.0,                        /* 15-16 */
                2.5, 4.0, 6.0, 9.0, 11.0,        /* 17-21 */
                14.0, 14.0, 16.0, 16.0, 17.0,    /* 22-26 */
                17.0, 18.0, 18.0, 18.0, 20.0     /* 27-31 */
                };
```

```
xsel_x_rotation( )
{
        if (x_rotation_index < 0 )      /* make sure index is within bounds */
                x_rotation_index = 0;
        if (x_rotation_index > 31 )
                x_rotation_index = 31;

x_midline = x_midline + x_rotation_table[x_rotation_index];
}

/*
 *      get_x_delta pulls x_delta out of a table based on the z position of the user.
 */ get_x_delta( )

{
static float z_xdelta_table[] = {
                5.5, 5.5, 5.5, 5.5, 6.0,          /* 35-39 */
                6.00, 6.75, 6.75, 7.0, 7.0, 7.33, /* 40-45 */
                7.33, 7.67, 7.67, 8.00, 8.50, 9.00, /* 46-51 */
                9.33, 9.67, 9.67, 10.0            /* 52-55 */
                };

int xd_index;

xd_index = z_position - 35;     /* use z_position to index into x delta table */ if (xd_index < 0)
                xd_index = 0;
        if (xd_index > 20 )
                xd_index = 20;

x_delta = z_xdelta_table[xd_index];     /* pull x delta out of table */
}

/*************************
 *      xsel_head_tilt computes how much the user's head has tilted (rotation about the
 *      z axis) since calibration and moves the x_midline accordingly.
 */
xsel_head_tilt( )

{
        head_tilt = tr_br_x - cal_tr_br_x;
        x_midline = x_midline + (head_tilt / 2.0);
}
/*
 *      absval returns absolute value of integer passed to it.
 *
 */
int absval(a)

int a;
{
        if (a < 0)
          return( 0 - a);
        else
          return(a);
}
```

We claim:

1. A system for computer vision based upon an image sensor that maps an image to memory cells to association with a computer comprising:

an object orientation and position patch for being attached to an object to be observed comprising a planar substantially nonreflective surface, at least three substantially coplanar and non-collinear reflective locations (a, b, and c) positioned upon the patch and a reflector (d) having the reflective properties of the surface of a regular curved surface intersecting the planar surface, an image sensor comprising means for generating a two-dimensional digital representation of the image stored in an array of memory cells arranged in a plurality of rows and column, each cell having an associated row and column address and being accessible for reading, a lens for focusing an image of the object including the orientation and position patch upon the image sensor, said lens defining an optical axis extending through the center of the lens and intersecting the image sensor near the center thereof, a light source fixed relative to the sensor and lens and being directed outwardly therefrom;

a computer having a processor and main memory, and means for reading the row and column addresses of the memory cells corresponding to the images (a′, b′, and c′) of reflective locations a, b, and c and an image (dls) of the light source reflected from the reflector d, and said computer having a task stored in main memory for detecting and quantifying a change in orientation and position of the object, said task detecting changes in the position along the optical axis and in directions perpendicular thereto by computing changes in the row and column addresses of the memory cells corresponding to the images a′, b′, and c′, and said task detecting change in rotation about axes perpendicular to the optical axes by computing differences in the row and column addresses of the memory cells corresponding to the image dls and the images a′, b′, and/or c′.

2. The system for computer vision according to claim 1 wherein the task stored in main memory for detecting and quantifying a change in orientation and position detects changes in the position along the optical axis by computing the average of the changes in distance between the addresses of images a′, b′, and c′ and interpreting a decrease in the average as a movement away from the lens.

3. The system for computer vision according to claim 1 wherein the task stored in main memory for detecting and quantifying a change in orientation and position detects changes in the positions perpendicular to the optical axis by computing the average of the changes in the row or column addresses of the images a′, b′, and c′.

4. The system for computer vision according to claim 1 wherein the task stored in main memory for detecting and quantifying a change in orientation and position detects changes in the rotation of the object about axes perpendicular to the optical axis by computing differences in the row or column addresses of at least one of the images a′, b′, c′ and the row or column address of image dls.

5. The system for computer vision according to claim 1 wherein the task stored in main memory for detecting and quantifying a change in orientation and position detects changes in the rotation about an axis parallel to the optical axis by observing the change in row or column addresses of at least one of the images a′, b′ and c′ and interpreting the direction of movements of said images as tangent to concentric circles about the axis of rotation.

6. The system for computer vision according to claims 1 to 5 wherein the image sensor comprises a solid-state image sensor having a two-dimensional array of light sensitive memory cells.

7. The system according to claim 1 having multiple light sources fixed relative to the sensor and lens and means for switching only one source on at one time.

8. The system according to claim 1 having multiple image sensors fixed relative to the light source and means for switching only one sensor on at one time.

9. A body pointer based upon an image sensor used in association with a computer comprising an orientation and position patch for being attached to the portion of the body used for pointing comprising a planar substantially nonreflective surface, at least three substantially coplanar and nonaligned reflective locations (a, b, and c) positioned upon the patch and a reflector (d) having the reflective properties of the surface of a regular curved surface mounted upon the planar surface, an image sensor comprising means for generating a two-dimensional representation of the image stored in an array of memory cells arranged in a plurality of rows and columns, each cell having an associated row and column address and being accessible for reading, a lens for focusing an image of the orientation and position patch upon the image sensor, said lens defining an optical axes extending through the center of the lens and intersecting the image sensor near the center thereof, a light source fixed relative to the sensor and lens and being directed outwardly therefrom, a computer having a processor and main memory, means for transferring to the computer the row and column addresses of the memory cells corresponding to the images (a′, b′, and c′) of reflective locations a, b, and c and an image (dls) of the light source reflected from the surface reflector d to the computer, said computer having a first task stored in main memory for calibrating the body pointer for an initial orientation and position of the pointer by recording the row and column addresses of the images a′, b′, c′ and dls, said computer having a second task stored in main memory for detecting and quantifying a change in orientation and position of the patch, said task detecting changes in the position along the optical axis and in direction perpendicular thereto by computing changes in the row and column addresses of the image a′, b′, and c′, and the task detecting the change in rotation about axes perpendicular to the optical axes by computing differences in the addresses of the image dls and images a′, b′, and/or c′.

10. The body pointer according to claim 9 wherein the task stored in main memory for detecting and quantifying a change in orientation and position detects changes in the position along the optical axis by computing the average of the changes in distance between the addresses of images a′, b′, and c′ and interpreting a decrease in the average as a movement away from the lens.

11. The body pointer according to claim 9 wherein the task stored in main memory for detecting and quantifying a change in orientation and position detects changes in the position perpendicular to the optical axis by computing the average of the changes in the row or column addresses of the images a', b', and c'.

12. The body pointer according to claim 9 wherein the task stored in main memory for detecting and quantifying a change in orientation and position detects changes in the rotation of the patch about axes perpendicular to the optical axis by computing differences in the row or column addresses of at least one of images a', b', c' and image dls.

13. The body pointer according to claim 12 wherein the task stored in main memory for detecting and quantifying a change in orientation and position detects changes in the rotation of the patch about an axis parallel to the optical axis by observing the change in row or column addresses of at least one of images a', b', and c' and interpreting the directions of movements of said images as tangent to concentric circles about the axis of rotation.

14. The body pointer according to claims 7 to wherein the image sensor comprises a solid-state image sensor having a two-dimensional array of light sensitive memory cells.

15. The body pointer according to claim 9 having multiple light sources fixed relative to the sensor and lens and means for switching only one source on at one time.

16. The body pointer according to claim 9 having multiple image sensors fixed relative to the light source and means for switching only one sensor on at one time.

17. An eyetracker based upon an image sensor used in association with a computer comprising
a display bearing indicia which may be selected with the user's eyes,
a head orientation and position patch for being attached to the face near an eye comprising a planar substantially nonreflective surface, at least three substantially coplanar and nonaligned reflective locations (a, b, and c) positioned upon the patch and a reflector (d) having the reflective properties of a regular curved surface mounted upon the planar surface,
an image sensor comprising means for generating a two-dimensional representation of the image stored in an array of memory cells arranged in a plurality of rows and columns, each cell having an associated row and column address and being accessible for reading,
a lens for focusing an image of the eye and the orientation and position patch upon the image sensor, said lens defining an optical axis extending through the center of the lens and intersecting the image sensor near the center thereof,
a light source fixed relative to the sensor and lens and being directed outwardly therefrom,
a computer having a processor and main memory,
means for transferring the row and column addresses of the memory cells corresponding to the images (a', b', and c') of reflective locations a, b, and c and an image (dls) of the light source reflected from the spherical surface reflector d and the row and column addresses of the image (cls) of the light source reflected from the cornea of the eye to the computer,
said computer having a first task stored in main memory or calibrating the eyetracker for an initial head orientation and position by recording the row and column addresses of the images a', b', c', dls and cls when the user gazes sequentially at least two of the indicia upon the display while the head is substantially immobile,
said computer having a second task stored in main memory for detecting and quantifying a change in orientation and position of the head, said task selecting changes in the position along the optical axis and in directions perpendicular thereto by computing changes in the row and column addresses of the images a', b', and c', and the task detecting the change in rotation about the axes perpendicular to the optical axes by computing differences in the addresses of the image dls and the images a', b', and c', and
said computer having a third task stored in main memory for correlating the row and column address of the corneal reflection image cls with indicia upon the display taking into consideration the instantaneous head position and orientation as determined by reference to the initial head orientation and position determined by the first task and the change in head position and orientation determined by the second task.

18. The eyetracker according to claim 17 wherein the task stored in main memory for detecting and quantifying a change in orientation and position detects changes in the position along the optical axis by computing the average of the changes in addresses between the images a', b', and c' upon the image sensor and interpreting a decrease in the average as a movement away from the lens.

19. The eyetracker according to claim 17 wherein the task stored in main memory for detecting and quantifying a change in orientation and position detects changes in the positions perpendicular to the optical axis by computing the average of the changes in the row or column addresses of the images a', b', and c'.

20. The eyetracker according to claim 17 wherein the task stored in main memory for detecting and quantifying a change in orientation and position detects changes in the rotation of the head about axes perpendicular to the optical axis by computing differences in the row or column addresses of at least one of images a', b', c' and image dls.

21. The eyetracker according to claim 17 wherein the task stored in main memory for detecting and quantifying a change in orientation and position detects changes in the rotation of the head about an axis parallel to the optical axis by observing the change in row, or column addresses of at least one of images a', b', and c' and interpreting the directions of movements of said images as tangent to concentric circles about the axis of rotation.

22. The eyetracker according to claims 17 to 21 wherein the image sensor comprises a solid-state image sensor having a two-dimensional array of light sensitive memory cells.

23. The eyetracker according to claim 17 having multiple light sources fixed relative to the sensor and lens and means for switching only one source on at one time.

24. The eyetracker according to claim 17 having multiple image sensors fixed relative to the light source and means for switching only one image sensor on at one time.

* * * * *

UNITED STATES PATENT AND TRADEMARK OFFICE
CERTIFICATE OF CORRECTION

PATENT NO. : 4,891,630

DATED : January 2, 1990

INVENTOR(S) : Mark B. Friedman and Gary J. Kiliany

It is certified that error appears in the above-identified patent and that said Letters Patent is hereby corrected as shown below:

In the Abstract Line 6 after "substantially" insert --nonreflective surface, at least three substantially--.

Column 2 Line 40 after "article" insert --cited in its--.

Column 3 Line 26 "a,, b,, and c," should read --a', b', and c'.--.

Column 3 Line 39 after "in" insert --main memory detects changes in positions perpendicular to--.

Column 4 Line 43 "orient" should read --orientation--.

Column 4 Line 52 "use" should read --used for--.

Column 9 Line 23 after "image" (first occurrence) insert --processing techniques to segment the reflective patch for--.

Column 9 Line 31 " ~ " should read -- > --.

Column 9 Line 65 after "image" insert --sensor and keyboard with an eye roughly centered in front--.

Column 10 Line 45 "y midline and x delta" should read --y_midline and x_delta--.

UNITED STATES PATENT AND TRADEMARK OFFICE
CERTIFICATE OF CORRECTION

PATENT NO. : 4,891,630

DATED : January 2, 1990

INVENTOR(S) : Mark B. Friedman and Gary J. Kiliany

It is certified that error appears in the above-identified patent and that said Letters Patent is hereby corrected as shown below:

Column 10 Line 47 "x midline" should read --x_midline--.

Claim 1 Line 25 Column 23 ":" should read --,--.

Claim 1 Line 39 Column 23 after "detecting" insert --the--.

Claim 5 Line 4 Column 24 "direction" should read --directions--.

Claim 9 Line 35 Column 24 "axes" should read --axis--.

Claim 11 Line 4 Column 25 "position" should read --positions--.

Claim 14 Line 23 Column 25 "7 to" should read --9 to 13--.

Claim 17 Line 69 Column 25 "or" should read --for--.

Claim 17 Line 3 Column 26 after "sequentially" insert --at--.

Claim 17 Lines 8-9 Column 26 "selecting" should read --detecting--.

Signed and Sealed this

Fourth Day of June, 1991

*Attest:*

*Attesting Officer*

HARRY F. MANBECK, JR.

*Commissioner of Patents and Trademarks*